United States Patent [19]

McEwen

[11] Patent Number: 4,605,010
[45] Date of Patent: Aug. 12, 1986

[54] PRESSURIZING CUFF

[75] Inventor: James A. McEwen, Richmond, Canada

[73] Assignee: Western Clinical Engineering Ltd., Richmond, Canada

[21] Appl. No.: 611,083

[22] Filed: May 17, 1984

[51] Int. Cl.[4] .............................................. A61B 17/12
[52] U.S. Cl. ..................................... 128/686; 128/327
[58] Field of Search ........ 128/686, 672, 677, 678–685, 128/327

[56] References Cited

U.S. PATENT DOCUMENTS

| 2,199,408 | 5/1940 | Liberte | 128/686 |
| 2,405,265 | 8/1946 | McAlpine | 128/686 X |
| 2,896,610 | 7/1959 | Speelman | 128/686 |
| 3,756,239 | 9/1973 | Smythe | 128/686 X |
| 3,765,405 | 10/1973 | Natkanski | 128/686 |
| 3,812,844 | 5/1974 | Sokol | 128/686 |
| 4,210,154 | 7/1980 | Klein | 128/686 X |
| 4,501,280 | 2/1985 | Hood, Jr. | 128/686 X |

OTHER PUBLICATIONS

Geddes et al.; "The Error in Indirect BP Measurement with the Incorrect Size of Cuff"; *Amer. Heart Journal,* vol. 96, No. 1, 7-1978, pp. 4–8.
McEwen et al.; "An Adaptive Tourniquet for Improved Safety in Surgery"; *IEEE Trans. on Biomed. Engineering,* vol. BME-29, No. 2, 2-1982, pp. 122-128.

*Primary Examiner*—Kyle L. Howell
*Assistant Examiner*—Angela D. Sykes

[57] ABSTRACT

A cuff which is useful for accurately, reliably and remotely determining the circumference of a limb which the cuff encircles. The cuff comprises a laminate consisting of a low-impedance conductor that does not vary significantly as a result of bending or flexing, and a high-impedance electrically conductive strip which is in electrical contact with the low-impedance conductor along its length, and which is comprised of a material that is sufficiently flexible to remain in electrical contact with the low-impedance conductor along its length while the conductor is bent or flexed; an electrically conductive contact; and, an elongated strip of flexible material to which the laminate and electrically conductive contact are attached, such that a voltage-dividing circuit may be formed when the cuff encircles the limb, the ratio of voltages being relative to the circumference of the limb and being insensitive to the impedance between the laminate and the electrically conductive contact.

18 Claims, 7 Drawing Figures

PRESSURIZING CUFF

FIELD OF THE INVENTION

This invention pertains to pressurizing cuffs for occluding and controlling blood flow into a human limb. The invention particularly pertains to a pressurizable cuff which conforms well to human limbs having different shapes including tapered shapes, and which provides information about the characteristics of the cuff and limb at the cuff site.

BACKGROUND OF THE INVENTION

It is well known to use an inflatable cuff to occlude blood flow into a human limb and to maintain such occlusion for an extended period to provide a bloodless surgical field in the portion of the limb distal to the cuff. It is also well known to employ an inflatable cuff to indirectly measure the blood pressure of a human by controlling blood flow into the patient's limb.

Human limbs may have an uneven or tapered configuration at any particular location along the limb. Most of the inflatable cuffs in the prior art do not conform well to the tapered non-cylindrical areas of limbs often subjected to occluding devices, resulting in the use of cuff pressures higher than actually required to obtain an occlusive effect for surgery due to the reduced effective area of contact between the cuff and the limb. The use of an unnecessarily high pressure and a cuff with a narrow effective area of contact is hazardous to the patient. Cuffs in the prior art which are intended to conform to a non-cylindrical shape, such as a tapered limb, do not tend to be adjustable over a range of tapered shapes and therefore the exact shape must be known or measured before selection and application of a cuff which will conform well to the tapered shape. This procedure is not practical and would require an unrealistically large inventory of cuffs. A mismatch of cuff shape and limb shape results in the patient being subjected to various hazards. One such hazard is a reduced effective area of contact between the cuff and limb which necessitates the use of higher and less safe inflation pressures to maintain a bloodless surgical field. Another hazard is an increased tendency of the cuff to creep down the patient's limb to a point where the surgical field may be obstructed or where the bladder may be fully distended without producing an occlusive effect. In some prior art cuffs there is an increased tendency for concentric layers to separate axially and 'telescope' down the patient's limb thereby losing the occlusive effect. Thus a larger volume must be filled with pressurized gas to initially occlude blood flow into the limb or to rapidly change the applied pressure in order to remain near the minimum safe pressure.

Prior art cuffs generally have only one means or dependent means for securing the cuff around the limb and the cuffs are rendered ineffective by a malfunction of the securing means. Many cuffs have materials and constructions which make the cleaning and reuse of the cuff difficult and time-consuming. Many are too expensive to make it feasible to consider disposal after a single use. Many of the prior art cuffs do not have inflatable bladders which completely encircle the limb. This is undesirable in surgical applications because greater displacements of the tissues beneath such cuffs may result and lead to injuries. Prior art cuffs have not been formed on or adjusted to a curved surface during fabrication and this may increase the likelihood that soft tissue beneath the cuff may be pinched or injured as the cuff is inflated, or that a separate bandage of soft material must be required beneath the cuff to reduce this pinching tendency. A bandage of this type may impair the effectiveness of the cuff and increases the complexity, time and cost of cuff application. No cuff known in the prior art contains means for determining the adequacy of the application to the limb so that the method of application may be adjusted or standardized in order for the cuff to be applied too loosely or too tightly, either of which may be hazardous.

The applicant is aware of the following U.S. patents which are more or less relevant to the subject matter of the applicant's invention.

| | | | |
|---|---|---|---|
| 3,756,239 | 9/1984 | Smythe | 128/327, 128/2.05C |
| 2,347,197 | 4/1944 | LaLiberte | 128/327 |
| 3,120,846 | 2/1964 | Fletcher | 128/327 |
| 3,570,495 | 3/1971 | Wright | 128/327 |
| 3,504,675 | 4/1970 | Bishop | 128/327 |
| 3,670,735 | 6/1972 | Hazlewood | 128/327 |
| 3,587,584 | 6/1971 | Keller | 128/327 |
| 3,977,393 | 8/1976 | Kovacic | 128/327 |
| 4,106,499 | 8/1978 | Ueda | 128/327 |
| 3,699,945 | 10/1972 | Hanafin | 128/2.05 C, 128/327 |
| 3,467,077 | 9/1969 | Cohen | 128/2.05 |
| 2,811,970 | 11/1957 | Hipps | 128/327 |

The following U.S. patent applications of the applicant are more or less relevant to the subject matter of the applicant's invention.

U.S. application Ser. No. 337,152; Title: Adaptive Pneumatic Tourniquet; Art Unit: 336; Inventor: McEwen.

U.S. application Ser. No. 451,610 Title: Pneumatic Tourniquet; Art Unit: 336; Inventor: McEwen.

U.S. application Ser. No. 375,557; Title: Occlusive Cuff; Art Unit: 335; Inventor: McEwen.

The applicant is also aware of the following published references which are more or less relevant to the subject matter of the applicant's invention.

J. A. McEwen and R. W. McGraw, "An adaptive tourniquet for improved safety in surgery,"IEEE Transactions in Bio-Medical Engineering, Vol. BME-29, February 1982, pp. 122–128.

L. A. Geddes and S. J. Whistler, "The error in indirect blood pressure measurement with the incorrect size of cuff," American Heart Journal, Vol. 96, 1978, pp. 4–8.

SUMMARY OF THE INVENTION

The invention is directed to a pressurizing cuff comprising means for encircling a human limb, means for causing pressure to be exerted on the limb beneath the cuff, and means for determining remotely information concerning the cuff and limb. Means are provided to enable the cuff to conform well to a limb having any of a wide range of shapes including non-cylindrical and tapered.

The cuff may include means for determining remotely the snugness of the cuff which encircles the limb, the taper of the limb encircled by the cuff, and the physical characteristics of the cuff.

The means for remotely determining the circumference of the limb may comprise graduations marked on the surface of the cuff. The means for remotely determining the circumference of the limb may consist of a laminate of low-impedance and high-impedance conductors such that a voltage-dividing circuit is formed when the cuff encircles the limb, the ratio of voltages being relative to the circumference of the limb.

The low-impedance conductor may comprise a malleable material such as nichrome wire which has an impedance which does not change significantly as a result of bending, moving and flexing of the cuff.

The high-impedance conductor may comprise an electrically conductive thermoplastic substance, such as a carbon impregnated electrically conductive thermoplastic substance.

The means for determining the degree of snugness of the cuff encircling the limb may comprise a pressure transducer such as a carbon impregnated thermoplastic foam with electrically conducting contacts. The contacts may be connected to apparatus which can determine the variable resistance of the foam as a function of the snugness of the cuff.

The means for remotely determining the taper of the limb encircled by the cuff may comprise graduations marked on a surface of the cuff in a manner such that the meeting angle of the two ends of the cuff encircling the limb is visible.

In a specific embodiment, the cuff comprises an inflatable bladder which completely encircles the limb, a stiffener which restrains the bladder about the limb circumference and causes the bladder to inflate inwardly, and a connector which rotates on a swivel fixture attached to the stiffener and which provides means for independently securing the bladder and the stiffener and for continuous adjustment of the bladder. The cuff may include graduations and electrical apparatus which provide information concerning the cuff and limb beneath the cuff.

GENERAL CHARACTERISTICS AND ATTRIBUTES OF THE INVENTION

The present invention provides an inflatable cuff which conforms much better to the shape of the patient's limb than prior art cuffs, and which provides information on the characteristics of the cuff and the limb beneath the cuff. This information permits identification of the width of the inflatable bladder in the cuff employed, the circumference of the patient's limb beneath the cuff, the shape of the patient's limb beneath the cuff, and the specific materials and structure of the cuff.

In applications involving the indirect measurement of a patient's blood pressure, the information obtained can be used to correct measurements of blood pressure for errors arising from variations in the measurement system.

In the prior art, the methods for determining the errors present in measurements of blood pressure made with inflatable cuffs are based in part on information concerning the type of cuff, the width of the bladder in the cuff, and the circumference and shape of the limb beneath the cuff. The present invention provides information which helps identify errors arising from cuff-related aspects of the measurement system and makes it possible to correct the measurements by either automatic or manual means.

In surgical applications the information obtained can be used in conjunction with knowledge about the patient's intraoperative blood pressure to adjust the pressure in the cuff to a level near the minimum safe pressure needed to maintain a bloodless surgical field.

Methods for calculating the minimum safe pressure for an inflatable cuff to maintain a bloodless field for surgery which have been described in the prior art require information on the specific type of cuff employed, the width of the bladder, the circumference of the limb beneath the bladder and the shape of the limb as well as information on the patient's intraoperative systolic blood pressure. The present invention conveniently provides some of the information needed for calculation of the minimum safe pressure either manually or automatically.

The cuff of this invention may be formed largely of thermoplastic synthetic resin materials which enable the cuff to be sterilized and placed close to the surgical site. The materials of construction are sufficiently inexpensive that the cuff may be discarded after a single use if desired.

The connector in one embodiment of the cuff swivels to enable the inflatable bladder to be secured while remaining in uniform contact around the entire circumference of a limb, which may be substantially cylindrical or conical in shape. The swiveling connector also enables the stiffener to be secured independently of the bladder while remaining in uniform contact with the bladder around the entire circumference of a cylindrical or tapered limb. The connector permits the cuff to be attached to a tapered limb without unduly obstructing potential surgical sites. The connector also permits the bladder to be continuously rather than discretely adjusted over a range of limb circumferences to ensure close conformance with the limb. This reduces the volume of pressurized gas needed to produce the desired effect and reduces any tendency of the cuff to roll down the limb when inflated. The connector and the swivel fixture may be formed to minimize any rotational moment which may tend to cause the stiffener to twist when the bladder is inflated. The connector may be formed to minimize any overlap which would bring it into direct contact with the limb.

The means included in the cuff for providing information on the cuff and limb may comprise means for determining the cuff type, the limb circumference, the tightness or looseness of cuff application on the limb, and the degree of non-cylindrical shape beneath the cuff. The means may permit determinations of cuff and limb characteristics to be made either visually by a person or remotely by electrical apparatus. The means for determining the cuff type, the limb circumference and the limb shape may be used in surgical applications to help determine the minimum safe pressure for inflation of the cuff in order to maintain a bloodless surgical field with minimum risk of injury to the patient. The cuff may also be used in applications where a patient's blood pressure is being measured to identify conditions where significant cuff-related errors may exist, and perhaps to correct the measured values of blood pressure. The means included in the cuff for providing information on how tightly or how loosely the cuff is applied to a patient's limb may be used to standardize the technique of cuff application or to dynamically adjust the application pressure so that it is within limits which enable the inflatable portion of the cuff to perform effectively when pressurized to occlude and control blood flow in the patient's limb. The means for providing information on the cuff and limb may be formed to be tolerant of wear, manufacturing variations, and varying electrical contact pressures due to factors such as movement, and may be formed so that they can be monitored throughout a surgical procedure or during a determination of blood pressure to promptly detect abnormal conditions.

BRIEF DESCRIPTION OF THE DRAWINGS

A specific embodiment of this invention has been chosen for purposes of illustration and description wherein.

DESCRIPTION OF THE SPECIFIC EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 4:
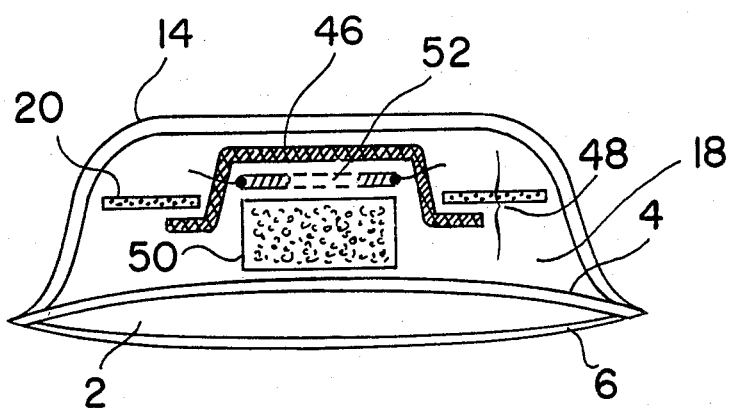
FIG. 4 is a sectional view taken along line 4—4 of FIG. 2.

The cuff of this invention, as can be seen in FIG. 4, includes an inflatable bladder 2 having side walls 4 and 6. Bladder 2 is closed along the ends and side walls 4 and 6 so as to be of gas-tight construction and may be formed in one integral piece or of two confronting pieces which are bonded together along their circumferential margins. To reduce pinching of the skin on the limb beneath the cuff, the two confronting pieces may be bonded on a curved surface having a radius approximating the average limb radius anticipated.

Figure 2:
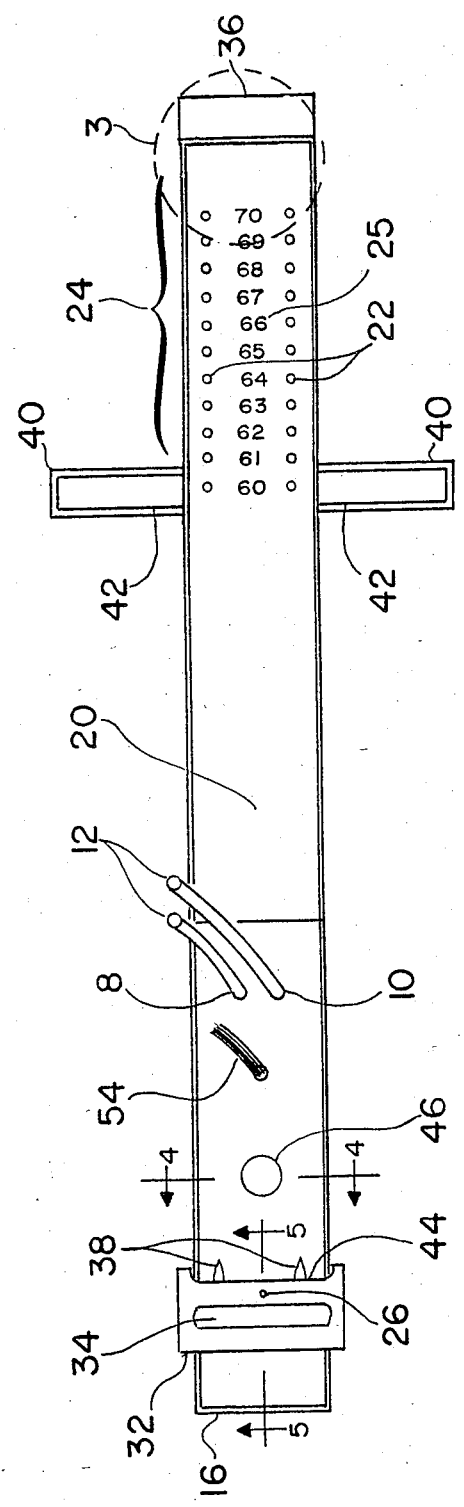
FIG. 2 is a side view of the cuff of FIG. 1 shown in its extended form.

As can be seen in FIG. 2, tubular ports 8 and 10 are secured to side wall 4 of the tube or alternatively are secured to a margin between side walls 4 and 6. Ports 8 and 10 define an inlet and an outlet for pressurized gas and a conduit for measuring the pressure of the gas in the bladder 2. Ports 8 and 10 are connected to tubing 12 through which pressurized gas is passed to and from the bladder 2 and through which the pressure in the bladder 2 is measured. Although pressurized gas is described in the specific embodiment, any pressurized fluid may be employed.

Covering approximately one-third of the outer surface of side wall 4, as can be seen in FIG. 4, is a wall part 14 which is bonded to side wall 4 along its edges and end 16 (visible in FIG. 2) to define a passage 18 extending along approximately one-third of the length of bladder 2. Wall part 14 and bladder 2 are preferably formed of a thermoplastic synthetic resin material such as polyethylene, polypropylene or nylon. Ports 8 and 10 are preferably of a stiffer construction and may be formed of a thermoplastic synthetic resin material.

Figure 1:
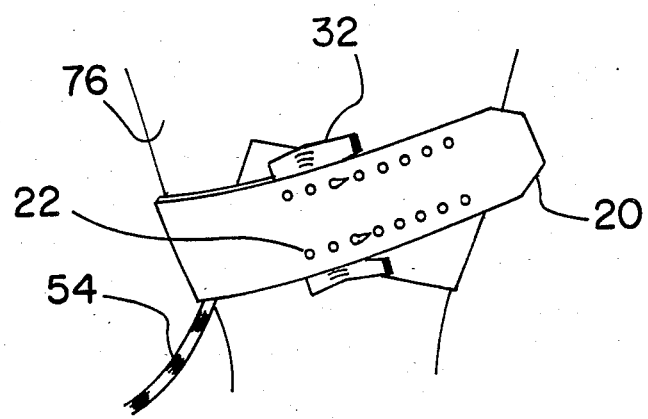
FIG. 1 is a perspective view of the cuff of this invention shown applied to the leg of a patient.
Figure 5:
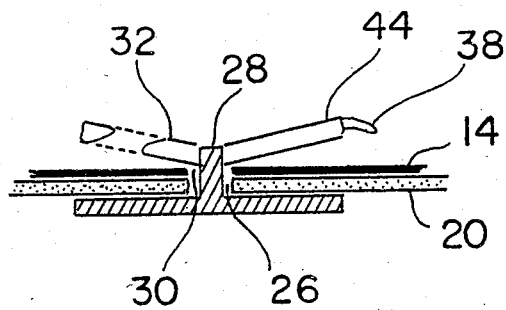
FIG. 5 is a sectional view taken along line 5—5 of FIG. 2 to better illustrate the construction of the connector of the cuff.

As can be seen in FIG. 2, a stiffener 20 is secured to bladder 2. Stiffener 20, which may be formed of a thermoplastic synthetic resin material, possesses sufficient flexibility to enable the stiffener to be wrapped smoothly about the limb of a patient and conform closely to the shape of the limb (as illustrated in FIG. 1) but is preferably otherwise unyielding, such as when placed in tension. A plurality of pairs of holes 22 spaced longitudinally at intervals of approximately one centimeter are formed in one end portion 24 of the stiffener 20. Near the opposite end of the stiffener 20 is a hole 26 to accommodate a pivot fixture 28 (see FIG. 5). Hole 26 in the stiffener 20 registers with opening 30 in wall part 14. Pivot fixture 28, which may be formed of a thermoplastic synthetic resin material, protrudes through hole 26 and opening 30 and serves to restrain connector 32 (see both FIGS. 2 and 5).

Connector 32 rotates laterally and vertically about the pivot fixture 28. Bladder 2 can be passed through a bevelled opening 34 in connector 32, pulled so that the bladder is in firm contact with the patient's limb around the entire circumference, and then folded back on itself and secured in position with fastener 36, which may be pressure-sensitive adhesive tape. After bladder 2 is secured, the stiffener 20 can be wrapped snugly around the patient's limb above the bladder 2 until an appropriate pair of holes 22 register with retaining pins 38, at which point the stiffener 20 is pulled down over the pins 38 to secure the stiffener 20. When the stiffener 20 has been secured, restraining straps 40 which are bonded to bladder 2 and contain fasteners 42 such as pressure-sensitive double-sided adhesive tape or VELCRO TM, may be folded over and fastened.

Connector 32 contains an electrically conductive strip 44 near the retaining pins 38 which comes into contact with a face of the stiffener 20 when it is secured by the pins 38. Connector 32 may be constructed from a stiff thermoplastic synthetic resin material and should be formed to minimize its height and thus its rotational moment. The connector 32 is also designed to be as narrow as possible while still allowing the bladder 2 to pass through it, and to have bevelled edges, in order to minimize the risk of injury to limb tissue of the patient.

A retaining cup 46 (as seen in FIG. 4) is secured to stiffener 20 approximately midway between connector 32 and ports 8 and 10, and serves to contain a pressure sensor 48 for measuring how tightly the cuff is in contact with the patient's limb. Pressure sensor 48 consists of carbon-filled plastic foam 50 which is in contact with a resistive carbon strip 52 connected at each end to electrical conductors forming part of cable 54 (see FIG. 2). Pressure sensor 48 thus consists of two parallel resistances wherein the resistance measured across strip 52 decreases as the pressure applied to foam 50 increases. A variety of other pressure sensors could be employed, but preferably the pressure sensor 48 should be constructed of inexpensive materials. Electronic device 68 (see FIG. 7) measures the resistance across strip 52 and produces an analog voltage proportional to the pressure for input to microcomputer 70.

Figure 3:
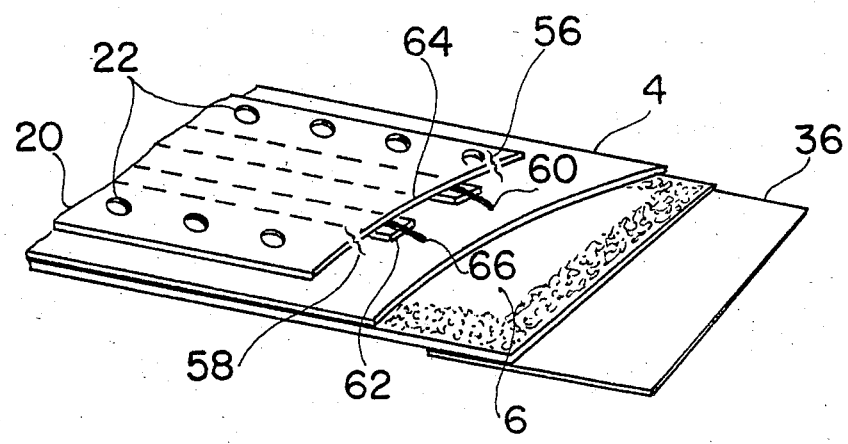
FIG. 3 is an enlarged detailed view of that portion of the cuff encircled by broken line 3 in FIG. 2, with portions thereof broken away to better illustrate the construction of the cuff.

Laminated strips 56 and 58 (see FIG. 3) extend between the pairs of longitudinally spaced holes 22 along the face of stiffener 20 which confronts bladder 2. Laminated strip 56 consists of a resistive material 60 which maintains a precise resistance despite bending (and may be formed of nichrome wire) in contact with another resistive material 62, which has a much higher resistance relative to material 60 but which need not retain a precise resistance. Resistive material 62 may be formed of VELOSTAT TM, a carbon impregnated electrically conductive thermoplastic substance manufactured by the 3M Company. Laminated strip 56 is secured to stiffener 20 with double-sided adhesive 64. Laminated strip 58 is of similar construction to laminated strip 56 except that material 66 may have a negligible electrical resistance and may be formed of fine wire.

Figure 6:
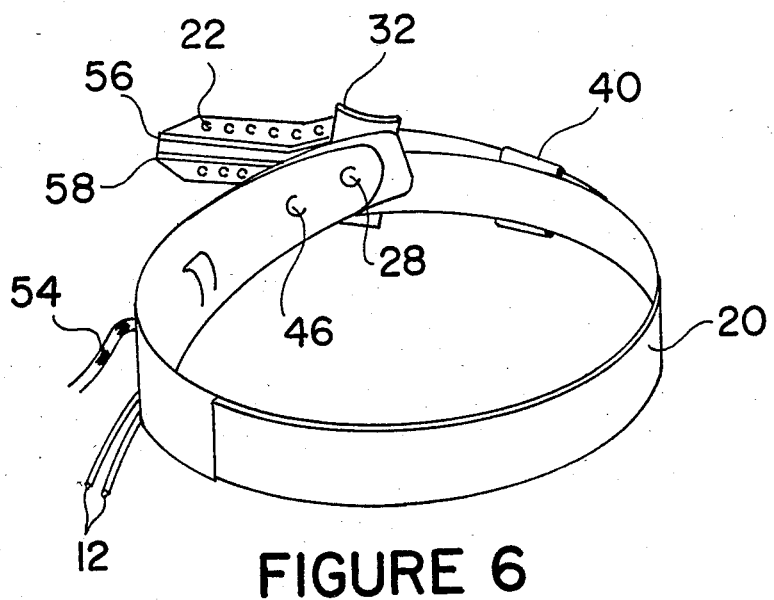
FIG. 6 is a perspective view of the cuff in its wrapped form.
Figure 7:
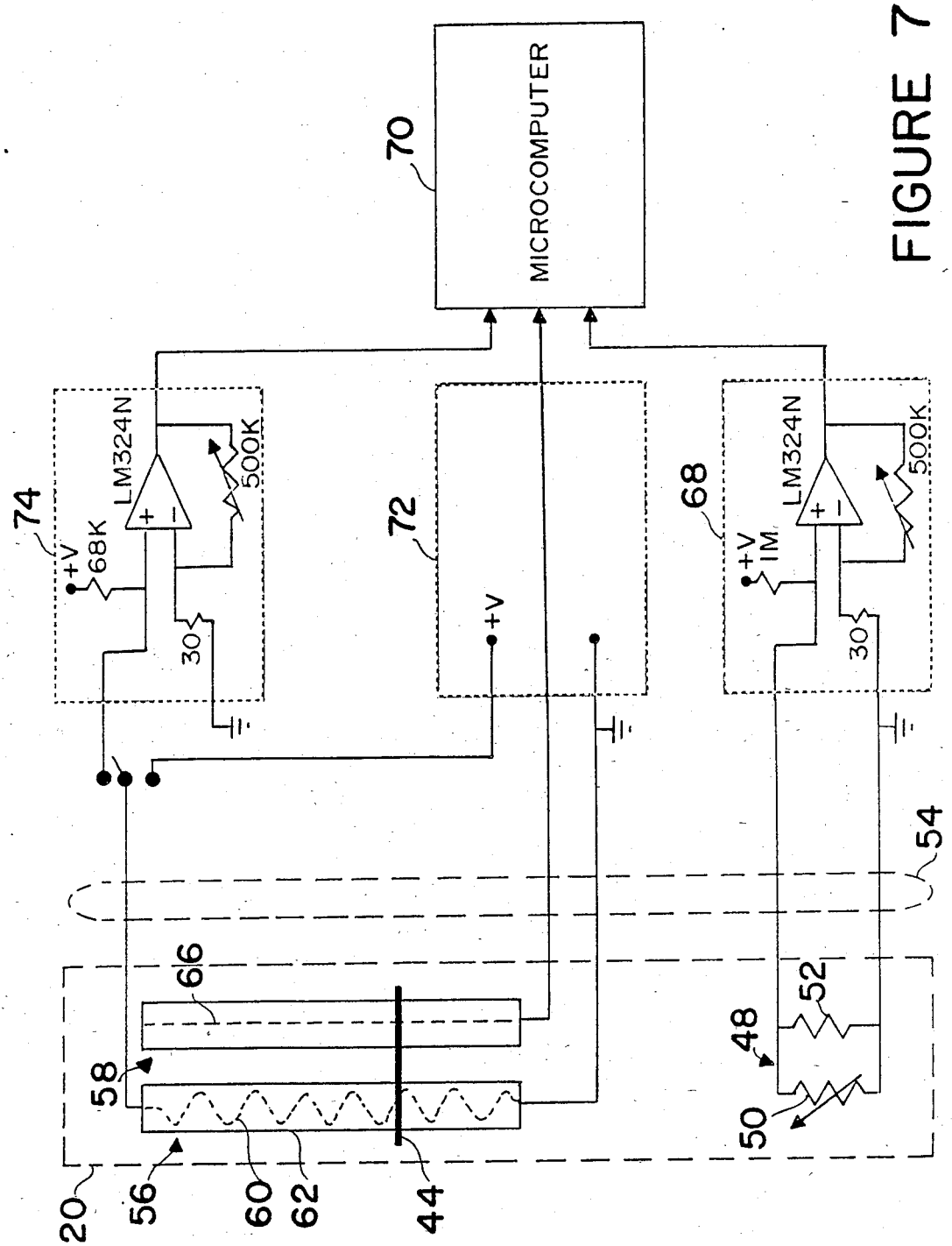
FIG. 7 is a schematic drawing of electronic circuitry connected to the cuff.

Electrical conductors forming part of cable 54 (see FIGS. 1 and 6) connect laminated strips 56 and 58 to electronic circuit 72 (see FIG. 7). Circuit 72 applies a known voltage across resistive material 60 and measures the voltage present at material 66 when conductive strip 44 is in contact with both laminated strips 56 and 58 at some position along their lengths. Thus laminated strips 56 and 58 form a voltage-dividing circuit when in contact with conductive strip 44, and the voltage measured at the high-impedance input of circuit 72 is representative of the circumference of the patient's limb around which the cuff is applied. Circuit 72 produces an analog voltage proportional to the circumference of the limb for microcomputer 70. The use of laminated strips 56 and 58 results in an accurate, reliable, and inexpensive measuring system which, because of the high resistances at the surface of the laminated strips, is electrically safe even when electrosurgical equipment is used while the cuff encircles the patient's limb. By employing a different resistive material 60 in each different type and size of cuff, each cuff can be uniquely identified by measuring the total resistance of conductive material 60 with resistance-measuring circuit 74. Although the voltage-dividing method for determining limb circumference is based on ratios of resistances in the specific embodiment, an equivalent voltage-dividing scheme based on ratios of capacitance or inductance might be employed.

To use this invention on the limb of a patient, a cuff having a size range which includes the size of the limb is selected and is connected to microcomputer 70. If desired, a soft protective bandage may be wrapped around the limb in typical fashion at the desired cuff location. The cuff is positioned at the desired location on the limb 76 (see FIG. 1) and preferably with connector 32 positioned as close to the trunk of the patient as possible and in a location readily accessible to the person applying the cuff. The cuff is then wrapped snugly about the limb, taking care to assure that both edges of bladder 2 are in contact with the limb around the entire circumference of the limb. Connector 32 is then rotated until opening 34 of the connector is approximately perpendicular to the end of the cuff. Bladder 2 is separated from the end portion 24 of the stiffener 20 and fastener 36 as the end of the bladder is passed through connector opening 34, pulled until the bladder 2 is in snug contact with the limb 76 as measured by pressure sensor 48 and indicated by microcomputer 70, and then secured on side wall 4 of the bladder so that both sections of bladder 2 are aligned where they overlap. After the bladder 2 is secured, the stiffener 20 is wrapped firmly over the bladder and connector 32 until a pair of holes 22 in the stiffener 20 register over retaining pins 38, at which point the stiffener 20 is first pushed down to cause the pins 38 to protrude through the holes 22 and is then pulled away from the connector 32 to secure the stiffener 20. The graduations 25 (see FIG. 4) on the stiffener 20 between the retaining pins 38 indicate the approximate limb circumference at the location of the cuff. Care is taken to assure that the stiffener 20 is positioned directly over the bladder 2 around the entire circumference of the limb 76, to prevent the bladder 2 from expanding to any great extent around the side edges of stiffener 20. Restraining straps 40 are then fastened tightly together to help hold the stiffener 20 in the proper position relative to the bladder 2. It should be noted that the bladder 2 and the stiffener 20 are secured independently of each other so that a malfunction of either the fastener 36 used to secure the bladder or the combination of retaining pins 38 and holes 22 used to secure the stiffener will not affect the other securing means, thus allowing the cuff to continue to function as desired.

When stiffener 20 is secured in position, microcomputer 70 can estimate the limb circumference and determine the type of cuff. This data can be used to adjust the pressure to which the cuff will be inflated. Information concerning how the pressure might be adjusted is given in the following references: J. A. McEwen and R. W. McGraw, "An adaptive tourniquet for improved safety in surgery," IEEE Transactions on Bio-Medical Engineering, Vol. BME-29, 1982, pp. 122–128; and J. A. Shaw and D. G. Murray, "The relationship between tourniquet pressure and underlying soft-tissue pressure in the thigh," Journal of Bone and Joint Surgery, Vol. 64A, 1982, pp. 1148–1152.

To inflate, the cuff ports 8 and 10 may be connected to tubing 12 through which pressurized gas is passed to and from the bladder 2. The pressure in the bladder can also be measured via tubing 12. Throughout the period of cuff inflation, microcomputer 70 can be programmed to continuously monitor the output of the pressure sensor, the limb circumference indicator, and the cuff type indicator to help promptly detect abnormal conditions such as the malfunction of a fastener and thus improve safety. It should be noted that when the cuff is wrapped around a cylindrical limb, circuit 72 indicates the actual limb circumference, but when the cuff is wrapped around a tapered limb, circuit 72 indicates approximately the mean limb circumference between the edges of the cuff. This difference is not significant for most limbs encountered in practice, and does not significantly affect the desired adjustment of cuff pressure. If desired, however, the degree of taper or conical shape of the limb can be measured by marking a protractor on the stiffener 20 at the connector 32, or can be measured remotely by adding a second potentiometer to the pivot fixture 28 and connector 32 to indicate the amount of rotation of the connector 32 from its normal position. Knowledge about the degree of tapered shape of the limb would permit the optimal cuff pressure to be determined more precisely.

To remove the cuff, the pressurized gas is first removed so that the bladder 2 of the cuff is deflated. Restraining straps 40 are then disengaged. Stiffener 20 is disengaged by first pulling it slightly toward the connector 32 and then pulling it up to remove retaining pins 38 from holes 22. The bladder 2 is disengaged by removing fastener 36 from the side wall of the bladder 2 and then pulling the free end of the connector back through the connector opening. The cuff can then be removed from the limb.

It is to be understood that the invention is not to be limited to the details herein given but may be modified within the scope of the appended claims.

I claim:

1. A cuff for encircling a human limb, comprising in combination:

(a) an inflatable bladder capable of completely encircling the limb;

(b) a stiffener which causes the bladder when encircling the limb to inflate inwardly;

(c) bladder-securing means for securing the bladder around the limb; and (d) stiffener-securing means for securing the stiffener around the limb independently of the bladder-securing means such that the bladder remains encircling the limb if either the bladder-securing means of the stiffener-securing means becomes ineffective.

2. A cuff as defined in claim 1 wherein the stiffener-securing means comprises a pivoting connector.

3. A cuff as defined in claim 2 wherein the pivoting connector is adapted to enable the bladder and the stiffener to conform closely to a range of tapered or cylindrical limbs.

4. A cuff which is useful for accurately, reliably and remotely determining the circumference of a limb which the cuff encircles, comprising:

(a) a laminate consisting of
  (i) a low-impedance conductor comprised of a material which has an impedance that does not vary significantly as a result of bending or flexing; and
  (ii) a high-impedance electrically conductive strip which is in electrical contact with the low-impedance conductor along its length, and which is comprised of a material that is sufficiently flexible to remain in electrical contact with the low impedance-conductor along its length while the conductor is bent or flexed;

(b) an electrically conductive contact; and (c) an elongated strip of flexible material to which the laminate and electrically conductive contact are attached, such that a voltage-dividing circuit may be formed when the cuff encircles the limb, the ratio of voltages being relative to the circumference of the limb and being insensitive to the impedance between the laminate and the electrically conductive contact.

5. A cuff as defined in claim 4 including means for determining remotely the snugness of the cuff which encircles the limb.

6. A cuff as defined in claim 5 wherein the means for determining the snugness of the cuff encircling the limb comprises a pressure transducer.

7. A cuff as defined in claim 6 wherein the pressure transducer consists of carbon impregnated thermoplastic foam with electrically conducting contacts.

8. A cuff as defined in claim 7 wherein the contacts are connected to apparatus which can determine the variable resistance of the foam as a function of snugness of the cuff.

9. A cuff as defined in claim 4 including means for determining remotely the taper of the limb encircled by the cuff.

10. A cuff as defined in claim 9 wherein the means for remotely determining the taper of the limb encircled by the cuff comprises a potentiometer forming part of a pivoting connector used to secure the cuff about the limb.

11. A cuff as defined in claim 9 wherein the means for remotely determining the taper of the limb encircled by the cuff comprises graduations marked on a surface of the cuff in a manner such that the meeting angle of the two ends of the cuff encircling the limb is visible.

12. A cuff as defined in claim 4 including means for identifying remotely the physical characteristics of the cuff.

13. A cuff as defined in claim 4 including means for applying pressure to the limb.

14. A cuff as defined in claim 4 wherein the low-impedance conductor is nichrome wire.

15. A cuff as defined in claim 4 wherein the high-impedance conductor comprises an electrically conductive thermoplastic substance.

16. A cuff as defined in claim 15 wherein the high-impedance conductor comprises a carbon impregnated electrically conductive thermoplastic substance.

17. A cuff as defined in claim 15 wherein the high-impedance conductor is a substance available under the trade mark VELOSTAT.

18. A cuff as defined in claim 4 wherein means for remotely determining the circumference of a limb are included and the means determines the circumference of the limb by calculating the ratio of the voltages in the voltage divider circuit.

* * * * *